US010980292B2

(12) United States Patent
Fan et al.

(10) Patent No.: US 10,980,292 B2
(45) Date of Patent: Apr. 20, 2021

(54) BRANCHED TUBE NETWORK AND TEMPERATURE REGULATING GARMENT WITH BRANCHED TUBE NETWORK

(71) Applicant: Cornell University, Ithaca, NY (US)

(72) Inventors: Jintu Fan, Ithaca, NY (US); Dahua Shou, Ithaca, NY (US); Huiju Park, Ithaca, NY (US)

(73) Assignee: Cornell University, Ithaca, NY (US)

( * ) Notice: Subject to any disclaimer, the term of this patent is extended or adjusted under 35 U.S.C. 154(b) by 343 days.

(21) Appl. No.: 16/073,700

(22) PCT Filed: Jan. 30, 2017

(86) PCT No.: PCT/US2017/015641
§ 371 (c)(1),
(2) Date: Jul. 27, 2018

(87) PCT Pub. No.: WO2017/132672
PCT Pub. Date: Aug. 3, 2017

(65) Prior Publication Data
US 2019/0045857 A1    Feb. 14, 2019

Related U.S. Application Data

(60) Provisional application No. 62/288,397, filed on Jan. 28, 2016.

(51) Int. Cl.
*H05B 1/02* (2006.01)
*A41D 13/005* (2006.01)
(Continued)

(52) U.S. Cl.
CPC ............ *A41D 13/005* (2013.01); *A61F 7/007* (2013.01); *A61F 7/02* (2013.01); *A61F 2007/006* (2013.01);
(Continued)

(58) Field of Classification Search
CPC ......... A41D 13/005; A61F 7/007; A61F 7/02; A61F 2007/006; A61F 2007/0076;
(Continued)

(56) References Cited

U.S. PATENT DOCUMENTS 4,738,119 A    4/1988 Zafred
4,998,415 A    3/1991 Larsen
(Continued)

FOREIGN PATENT DOCUMENTS

| CN | 1404805 A | 3/2003 |
|---|---|---|
| CN | 204930447 U | 1/2016 |
| WO | 2015/148411 A1 | 10/2015 |

*Primary Examiner* — Mark H Paschall
(74) *Attorney, Agent, or Firm* — Hodgson Russ LLP

(57) ABSTRACT

In an embodiment of the present disclosure, a garment for regulating a temperature of a wearer is provided. The garment includes a fabric configured to be worn by the wearer. The fabric includes channels parallel to a primary surface of the fabric. The garment includes a branched tube network for circulating a working fluid. The branched tube network is disposed in the channels of the fabric. The branched tube network includes a plurality of tubes wherein at least one end of each tube of the plurality of tubes is branched and connected to two daughter tubes, or more, the connection having a branch angle of between 1 and 359 degrees, inclusive. The tube network has at least two levels of branches.

25 Claims, 17 Drawing Sheets

(51) Int. Cl.
*A61F 7/02* (2006.01)
*A61F 7/00* (2006.01)

(52) U.S. Cl.
CPC ........... *A61F 2007/0076* (2013.01); *A61F 2007/0086* (2013.01); *A61F 2007/0093* (2013.01); *A61F 2007/0096* (2013.01); *A61F 2007/0233* (2013.01); *A61F 2007/0234* (2013.01)

(58) Field of Classification Search
CPC ........ A61F 2007/086; A61F 2007/0093; A61F 2007/0233; H05B 1/02; H05B 3/34; H05B 3/342; H05B 3/347
USPC ................... 219/211, 213, 529, 494
See application file for complete search history.

(56) References Cited

U.S. PATENT DOCUMENTS

| | | | |
|---|---|---|---|
| 8,465,351 B2 | 6/2013 | Smith et al. | |
| 2008/0306433 A1 | 12/2008 | Cesaroni | |
| 2012/0053661 A1* | 3/2012 | Hooper | A61F 7/02 607/104 |

* cited by examiner

Front  Back

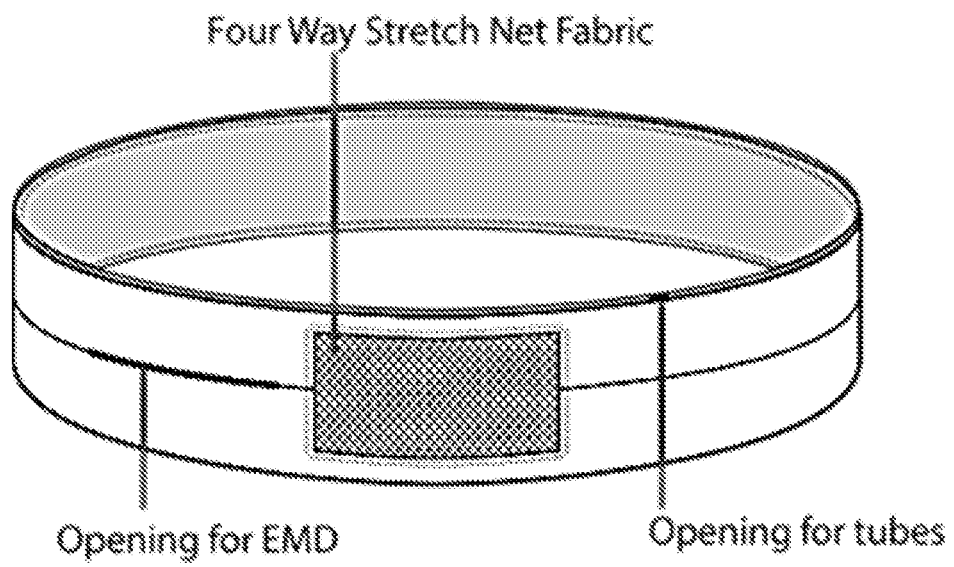
Fig. 30
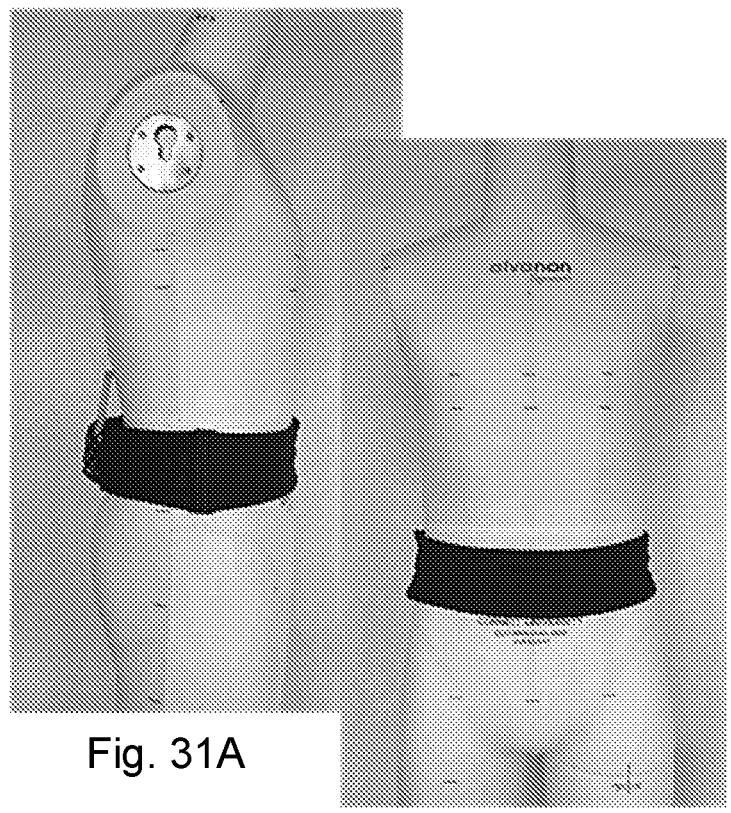
Fig. 31A
Fig. 31B

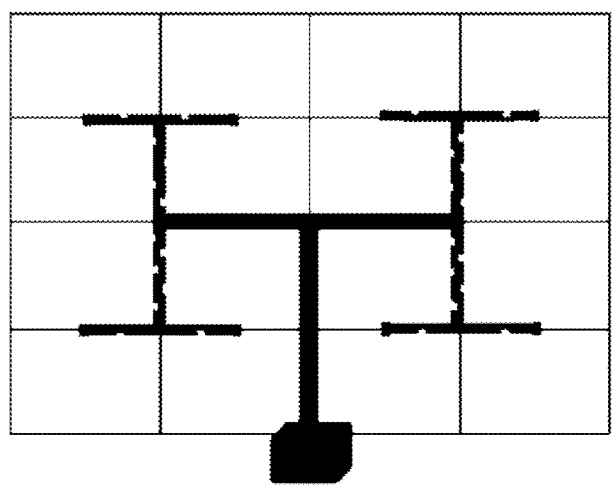
Fig. 32
 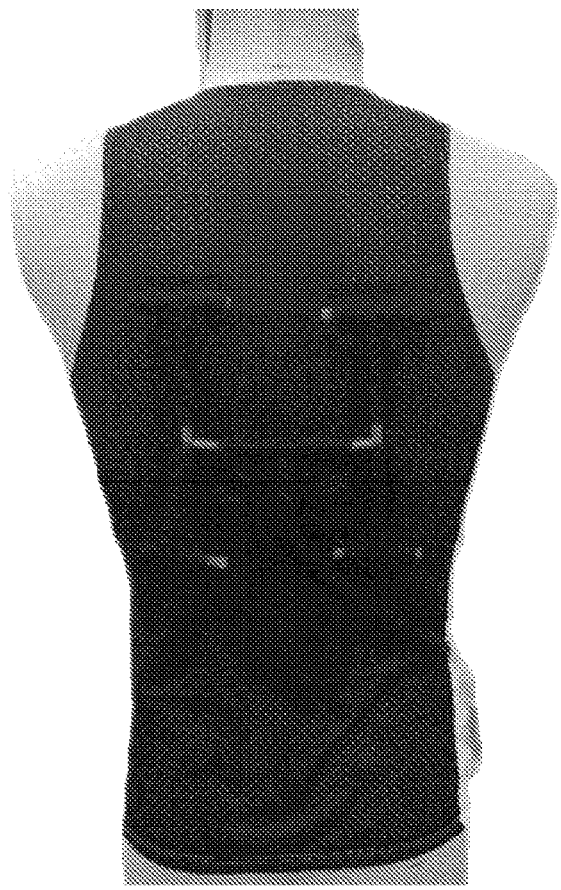
Fig. 33A　　　　　　　　　　　Fig. 33B

BRANCHED TUBE NETWORK AND TEMPERATURE REGULATING GARMENT WITH BRANCHED TUBE NETWORK

CROSS-REFERENCE TO RELATED APPLICATIONS

This application claims priority to U.S. Provisional Application No. 62/288,397, filed on Jan. 28, 2016, the disclosure of which is incorporated herein by reference.

STATEMENT REGARDING FEDERALLY SPONSORED RESEARCH

This invention was made with government support under contract no. DE-AR0000528, OSP 74585 awarded by the Department of Energy. The government has certain rights in the invention.

FIELD OF THE DISCLOSURE

The present disclosure relates to garments for regulating temperature.

BACKGROUND OF THE DISCLOSURE

Clothing may be considered a portable environment or a second skin. If clothing can be made to possess a thermal regulatory function, for example, providing cooling when the wearer feels hot and heating when the wearer feels cold, it can help with survival in extreme environments, improve comfort in moderate thermal conditions, and save significant energy when heating and cooling a larger space.

One of the most effective ways of providing heating or cooling to the wearer is to distribute/circulate warm or cool fluid in the microclimate next to skin. If the next-to-skin temperature is too high, a cool fluid is distributed/circulated through fine tubes embedded in the clothing; if the next-to-skin temperature is too low, warm fluid is distributed through fine tubes embedded in the clothing. The fluid can be, for example, one or more liquids and/or gases. For example, the fluid may be air.

In so distributing/circulating a fluid, it is advantageous to minimize pressure drop or pumping power. There is a long-felt need to minimize the pressure drop caused by the distribution network (e.g., tubes), while maintaining the effectiveness of heat transfer.

BRIEF SUMMARY OF THE DISCLOSURE

The present disclosure provides a branched tube network embedded in a garment. An objective of the present disclosure is to reduce pressure drop or power consumption in air/fluid flow through the tubes of the tube network, while distributing the fluid to a large area of the garment. The presently disclosed branched network has the advantage that local blocking or compression of tubes within the tube network may not affect working fluid delivery throughout the entire network.

In an embodiment of the present disclosure, a garment for regulating a temperature of a wearer is provided. The garment includes a fabric configured to be worn by the wearer. The fabric includes channels parallel to a primary surface of the fabric. The garment includes a branched tube network for circulating a working fluid. The branched tube network is disposed in the channels of the fabric. The branched tube network includes a plurality of tubes wherein at least one end of each tube of the plurality of tubes is branched and connected to at least two daughter tubes, the connection having a branch angle of between 1 and 359 degrees, inclusive. The tube network has at least two levels of branches. In an exemplary embodiment, each tube is connected to two daughter tubes.

In another aspect of the present disclosure, a branched tube network for a temperature regulating garment is provided. The branched tube network includes a parent tube with a branched end. The branched tube network also includes at least two daughter tubes, each daughter tube having a first end and a branched end. The first end of each daughter tube is connected to the branched end of the parent tube. The branched tube network includes at least two sets of at least two granddaughter tubes, each granddaughter tube having a first end connected to the branched end of a respective daughter tube. In this way, the branched end of each daughter tube is connected to a set of at least two granddaughter tubes. The present disclosure may be embodied as a garment for regulating a temperature of a wearer made using this branched tube network.

DESCRIPTION OF THE DRAWINGS

For a fuller understanding of the nature and objects of the disclosure, reference should be made to the following detailed description taken in conjunction with the accompanying drawings, in which:

FIG. 30 is a diagram depicting a waist band according to another embodiment of the present disclosure;

FIG. 31A shows a side view of a waistband according to another embodiment of the present disclosure;

FIG. 31B is a front view of the waistband of FIG. 28A;

FIG. 32 shows a branched tube network of the present disclosure, wherein the tubes are connected at 180 degrees and the tubes are perforated;

FIG. 33A shows a front view of an exemplary undershirt according to another embodiment of the present disclosure, wherein the tube network includes tubes connected at 180 degrees (T-shaped connections);

FIG. 33B is a rear view of the undershirt of FIG. 33A;

DETAILED DESCRIPTION OF THE DISCLOSURE

Figure 2:
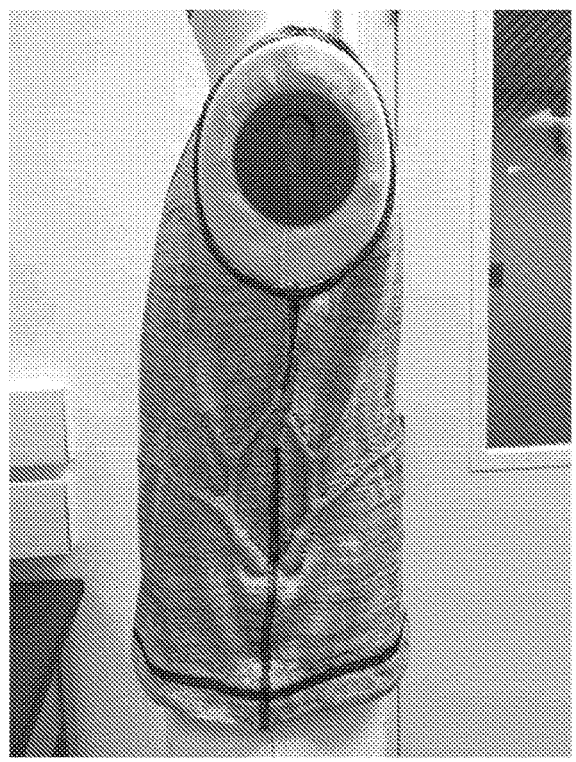
FIG. 2 shows an undershirt having an embedded tube network of the present disclosure.
Figure 3:
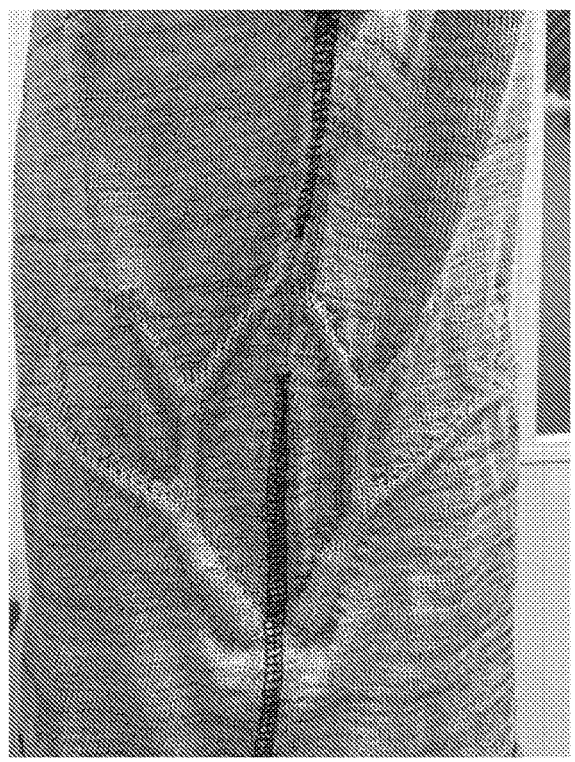
FIG. 3 shows a detailed view of the embedded tube network in FIG. 2.

A temperature-regulating garment system is disclosed herein. The system comprises a tube network, an electromechanical device (EMD), and a sensing and control unit (controller). The EMD may further comprise a thermoelectric energy conversion unity (energy conversion device) and a blower. The present disclosure will be described by way of exemplary garments, for example, a shirt, however, the scope of the disclosure should not be limited to such examples. One having skill in the art will understand that the present disclosure can be embodied in other garments, etc. FIGS. 2 and 3 show an exemplary embodiment of a knit undershirt incorporating an embedded tube network of the present disclosure.

Figure 1:
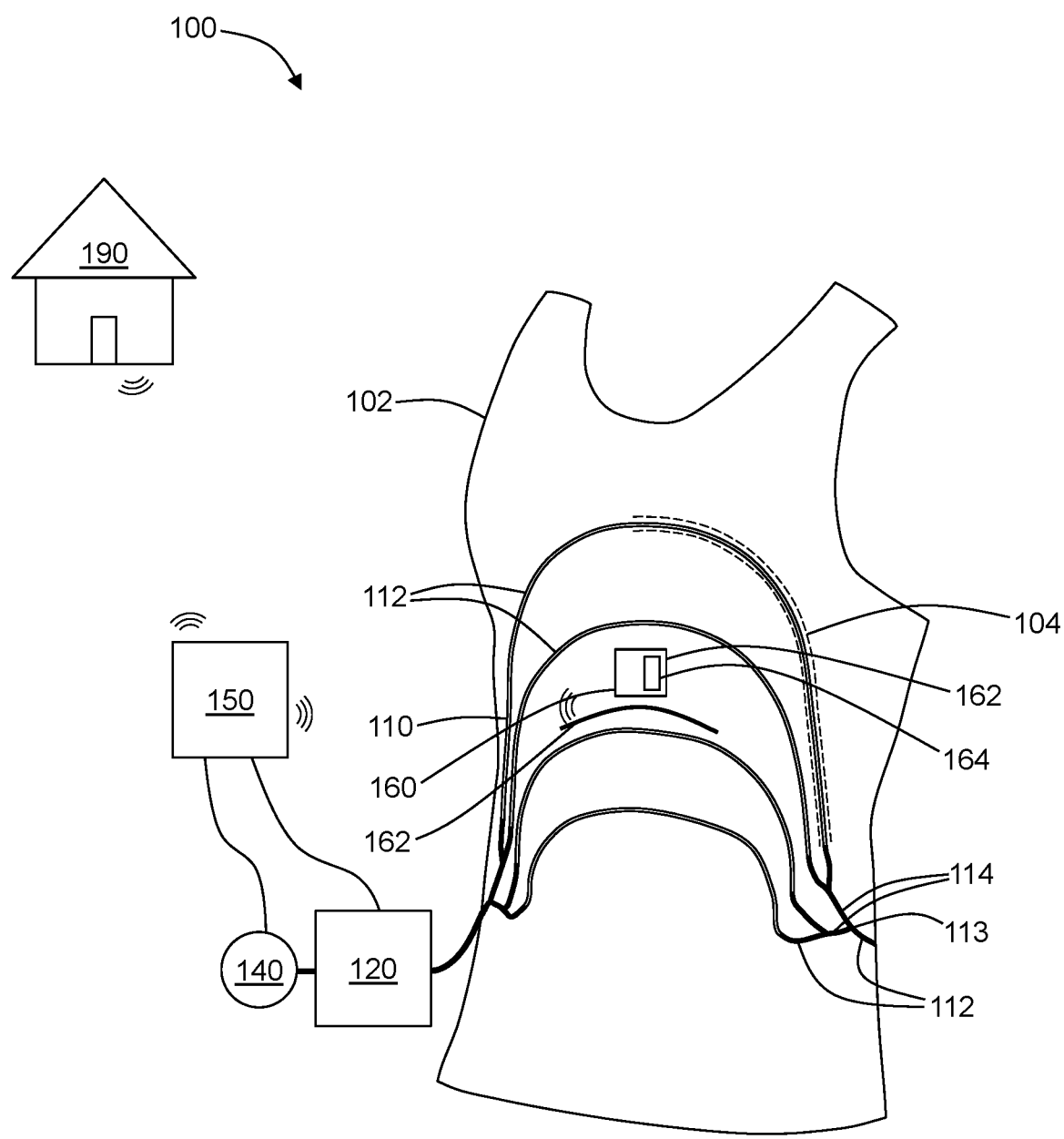
FIG. 1 shows a garment according to an embodiment of the present disclosure.

In an aspect, the present disclosure may be embodied as a garment 100 for regulating a temperature of a wearer (see, e.g., FIG. 1). The garment 100 includes a fabric 102 configured to be worn by the wearer. The fabric 102 includes channels 104 running parallel to a primary surface of the fabric 102. A channel may be formed between layers of the fabric 102 (where the fabric is multi-layered). A channel may be formed by attaching additional fabric to an outside surface or an inside surface of the fabric. A channel may be formed through the use of other attachments such as, for example, rings, hooks, fasteners, stitches, or other techniques for affixing tubes to the fabric of a garment.

The garment 100 further comprises a branched tube network 110 made up of a plurality of tubes 112. At least a one end 113 of each tube 112 of the plurality of tubes is branched and connected to at least two daughter tubes 114. The tube network 110 has at least two levels of branches. In other words, where a tube (considered a parent tube) is branched and connected to at least two daughter tubes is a level, and where a daughter tube is, in turn, branched and connected to at least two daughter tubes is a second level g. As such, each daughter tube may also be consider to be a parent tube (with respect to the further daughter tubes to which it is connected).

In some embodiments, each tube 112 is bifurcated and connected to two daughter tubes 114. In such embodiments, the connection from the "parent" tube 112 to the two daughter tubes 114 results in a branch angle θ between the daughter tubes 114. The branch angle θ is between 1 and 359 degrees, inclusive. In some embodiments, the branch angle θ is between 30 degrees and 60 degrees, inclusive. In some embodiments, the branch angle is 35, 40, 45, 50, 55, 90, 120, 150, or 180 degrees. The branch angle θ may be analytically determined as further described below. In this way, the bifurcation of the parent tube to two daughter tubes is akin to dichotomous branching. The exemplary embodiments wherein a tube is bifurcated (branched into two) are used throughout the remainder of the present application (including the drawings) for convenience, and the disclosure should not be limited to only such bifurcated embodiments unless expressly stated.

Each parent tube (i.e., each branched tube) may have a diameter greater than the corresponding connected daughter tubes. For example, the diameter of a daughter tube may be between 60% and 80%, inclusive, of a diameter of a corresponding parent tube. In other embodiments, the diameter of a daughter tube may be 65%, 70%, or 75% of the diameter of the corresponding parent tube. In other embodiments, the ratio of the daughter tube diameter to the parent tube diameter may be analytically determined as further described below.

Figure 5:
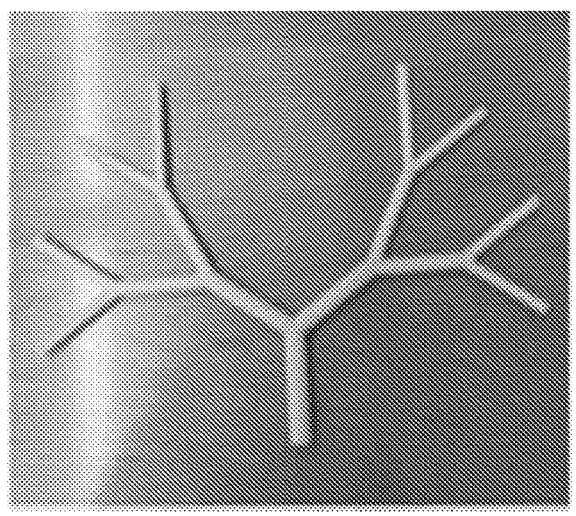
FIG. 5 shows an exemplary embodiment of a tube network of the present disclosure fabricated by 3D printing using a hard material (ABS plastic)
Figure 6:
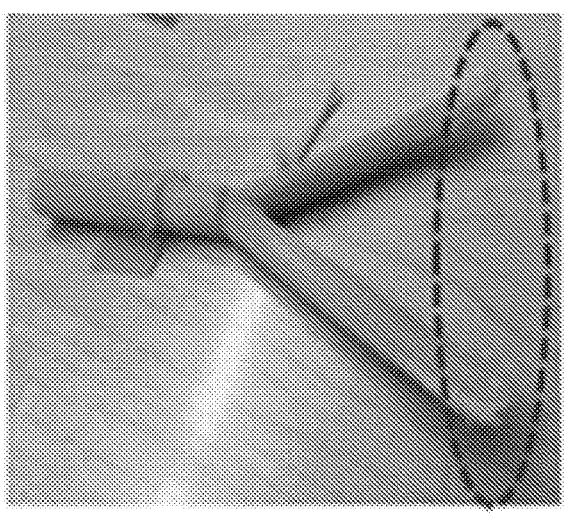
FIG. 6 shows an exemplary embodiment of a portion of a tube network of the present disclosure fabricated by 3D printing using a soft material (Ninja Flex®)
Figure 7:
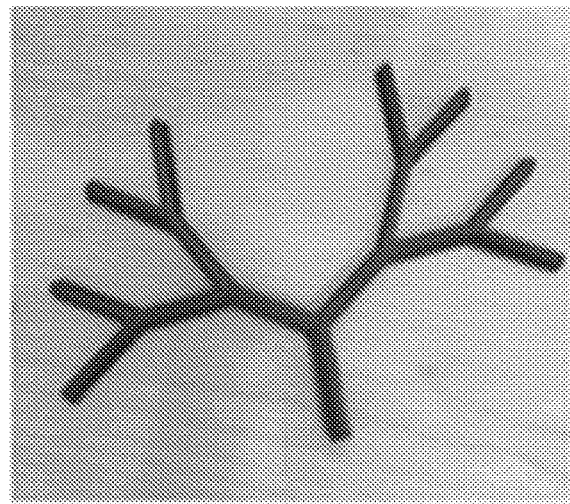
FIG. 7 shows an exemplary embodiment of a tube network of the present disclosure fabricated by 3D printing with added supporting material.
Figure 9:
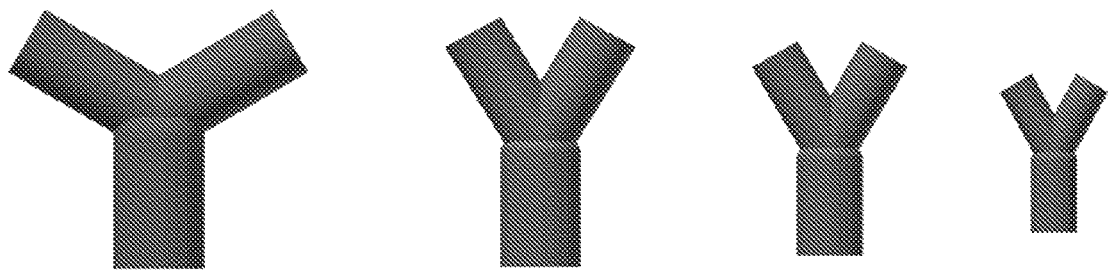
FIG. 9 depicts Y-shaped tube connectors having varying sizes and connection angles.
Figure 10:
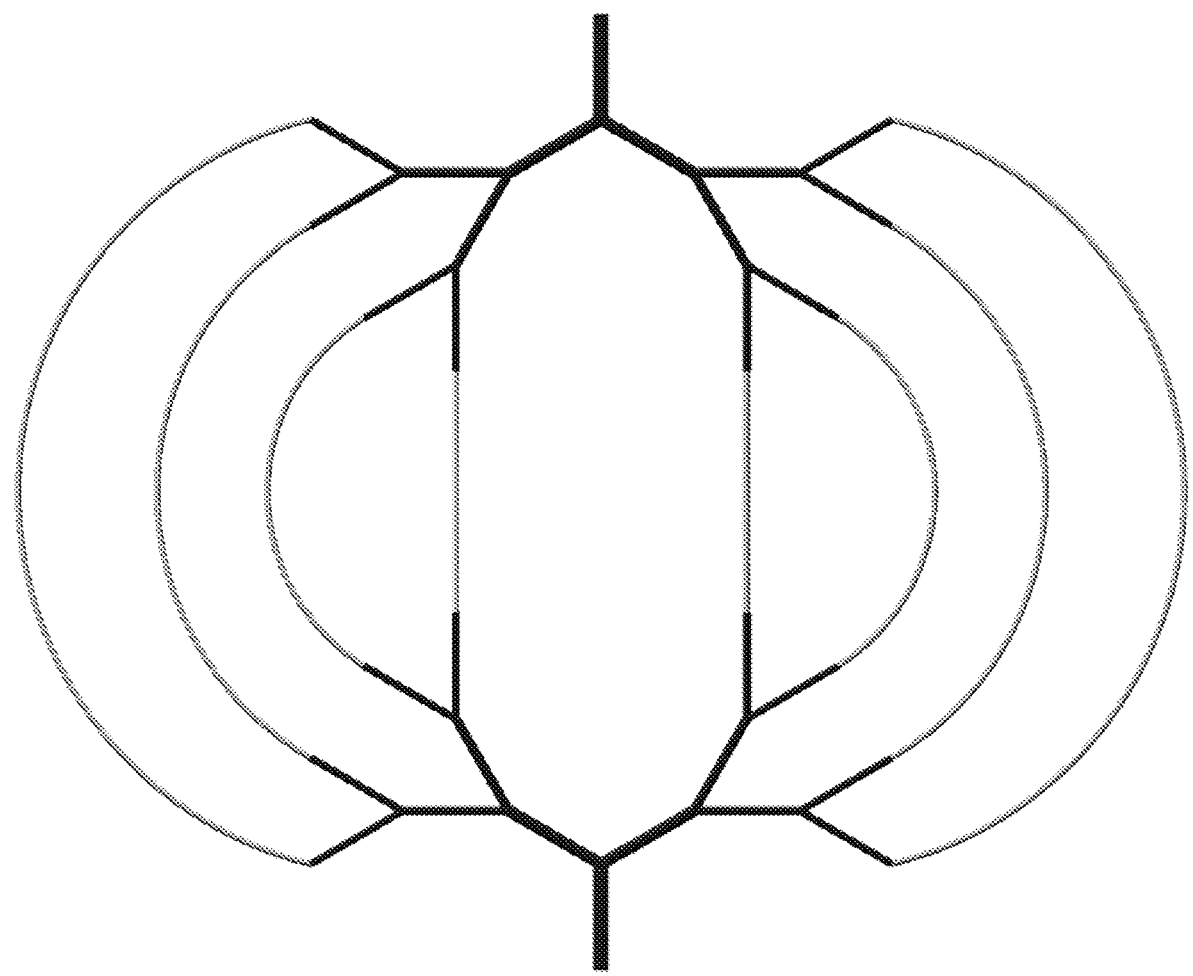
FIG. 10 shows an exemplary symmetric discharge-collect tube network.
Figure 11:
FIGS. 11 and 12 show an exemplary garment having an embodiment of the presently-disclosed tube network.
Figure 12:
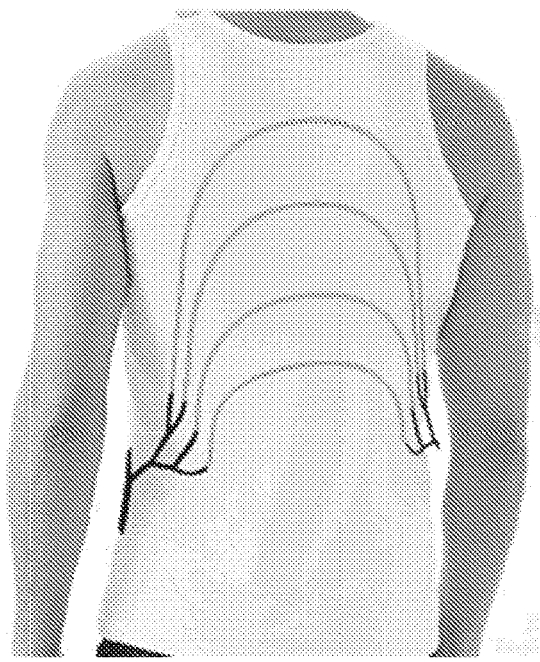

The branched tube network 110 may be fabricated through the use of 3D printing, molding, extrusion of separate components, or other techniques known for fabricating such devices. The tube network 110 may be made from rigid materials (for example, ABS plastic—see FIG. 5), flexible materials (for example, polyurethane—see FIG. 6), or combinations of materials (for example, a flexible polyurethane with structure support using ABS—see FIG. 7). The tube network 110 may be fabricated using a plurality of tubes interconnected using Y-shaped pieces as depicted in FIG. 9. In some embodiments, the tubes of the tube network may be perforated (i.e., having holes) such that the working fluid, for example, air, may be exhausted at multiple locations along the length of the tubes.

Figure 4:
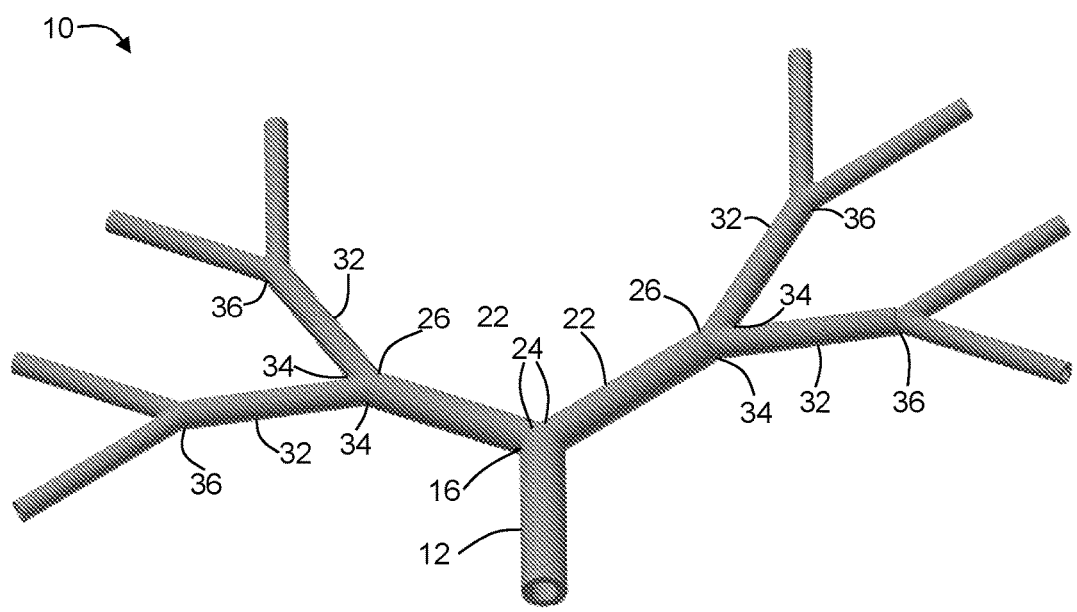
FIG. 4 shows an exemplary embodiment of a tube network according to the present disclosure.

With reference to FIG. 4, the branched tube network 10 may also be described as having a parent tube 12 with a branched end 16. At least two daughter tubes 22 each have a first end 24 connected to the branched end 16 of the parent tube 12. Each daughter tube 22 having a branched end 26. At least two sets of at least two granddaughter tubes 32 each have a first end 34 connected to the branched end 26 of a respective daughter tube 22. In this way, the branched end 26 of each daughter tube 22 is connected to a set of at least two granddaughter tubes 32. In some embodiments, the parent tube 12 is bifurcated and connected to two daughter tubes 22 and each daughter tube is bifurcated and connected to two granddaughter tubes 32. The diameter of the parent tube 12 may be greater than the diameter of the daughter tubes 22. Similarly, the diameter of the daughter tubes 22 may be greater than the diameter of the granddaughter tubes 36.

The garment 100 may further comprise an energy conversion device 120 for heating and/or cooling the working fluid. The energy conversion device 120 is in fluidic communication with the tube network 110. For example, the energy conversion device 120 may be connected to a primary tube of the plurality of tubes 112 (i.e., an unconnected end of a parent tube) such that working fluid, for example, air, is heated or cooled before transiting the tube network 110. The garment 100 may further comprise a blower 140 (sometimes called a pump) for moving the working fluid through the tube network. The blower 140 is in fluidic communication with the energy conversion device 120 and the branched tube network 110.

In some embodiments, the blower 140 is worn under by the wearer under the fabric 102. For example, the blower 140 may be attached to the wearer using a waist belt, garter belt, or the like. In some embodiments, the garment has a pocket, and the blower is disposed in the pocket. The garment 100 may further comprise a mesh configured to cooperate with an intake 142 of the blower 140. In this way, the intake 142 of the blower 140 can receive ambient air such that air may be used as the working fluid. The mesh may be a loose weave of fabric, a fabric woven to have holes, a material having holes therethrough, and/or other material through which air may move with less restriction than the fabric 102. (The blower and energy conversion device may be referred to herein as the electromechanical device or "EMD.")

The garment 100 may further comprise a controller 150 in electronic communication with the blower 140. The controller 150 is configured to control the blower 140. For example, the controller 150 may be configured to adjust the speed of the blower 140 to move more or less working fluid through the tube network 110. Similarly, the controller 150 may be in electronic communication with the energy conversion device 120 to control the energy conversion device 120. For example, the blower 140 may be configured to adjust a heating or cooling output of the energy conversion device 120. The controller 150 may be configured to communication with an environmental system 190. Such an environmental system 190 may be a system that does not make up a portion of the garment. Rather, the environmental system 190 may be a building system, such as, for example, a heating, ventilation, and air conditioning (HVAC) system of a building. In this way, the controller 150 of the garment 100 may adjust its regulation based on signals received from the environmental system 190. In a particular example, if a building HVAC system indicates that the air conditioning has been turned off for the evening, a controller may adjust the blower and/or energy conversion device in anticipation of the cooling needs of the wearer.

The garment 100 may further include one or more sensors 160 in electronic communication with the controller 150. The controller 150 may be configured to control the blower 140 based on a signal received from the one or more sensors 160. In some embodiments, a sensor of the one or more sensors 160 is a temperature sensor 162. The temperature sensor 162 may be configured to be positioned near the skin of the wearer. A sensor comprises a passive wireless circuit 164. For example, a temperature sensor 162 comprises a passive circuit 164 wirelessly energized using radio frequency (RF) energy. For example, the passive circuit may be configured to be powered in a manner similar to an RFID device. The passive circuit 164 may include an RF antenna 166 affixed to the fabric 102. In some embodiments, the RF antenna 166 is embroidered onto the fabric 102.

Tube Network

A branched network of the present disclosure comprises a network of "parent" tubes and "daughter" tubes, wherein each parent tube branches into two or more daughter tubes. In turn, daughter tubes may branch into two or more additional daughter tubes (in this case, a daughter tube may be considered a parent tube with respect to the additional daughter tubes). It should be noted that, although reference is made to a parent tube branching into daughter tubes, this can also be considered as daughter tubes combining into a parent tube.

Figure 8:
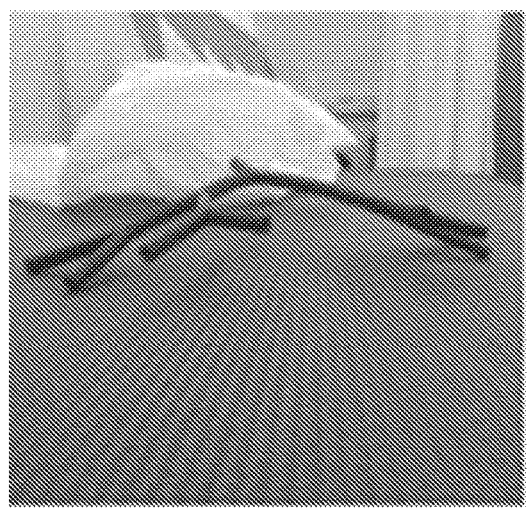
FIG. 8 shows an exemplary embodiment of a tube network of the present disclosure fabricated by 3D printing and then further modified to provide a curvature to the tube network to better conform to a shape of the wearer.

Such a branched tube network can be fabricated in any way. For example, the branched network of tubes can comprise tubes joined by Y-shaped connectors (such as those shown in FIG. 9), the network can be 3D-printed (such as the examples shown in FIGS. 5-8), the network can be molded, etc. In some embodiments, the branched tube network is configured to have a curvature such that the network conforms to the shape of a body, for example, as shown in FIG. 8.

The tube network may have any orientation. For example, warm/cool fluid may be supplied from a bottom parent tube and distributed upwards to the branched daughter tubes. Other embodiments may have parent tubes in a top configuration, side configuration (see, e.g., FIGS. 11 and 12), or other orientations as will be apparent in light of the present disclosure. In FIGS. 4-5, 7-8, and 10-12, each exemplary tube network is shown as having three levels of branches (i.e., branch number N=3), where a parent tube branches into daughter tubes. Other embodiments may have fewer or additional levels of branches, selected according to the desired application.

There are advantageous ratios between the diameters of the daughter tubes ($d_{k+1}$) and parent tubes ($d_k$) for minimum pressure drop or power consumption in various configurations. For example, in a bifurcated network with laminar flow, an advantageous diameter ratio has been determined to be $d_{k+1}/d_k=0.7937$ with the branch number N=2, or $d_{k+1}/d_k=0.6934$ with the branch number N=3. In a bifurcated network with turbulent flow, an advantageous diameter ratio has been determined to be $d_{k+1}/d_k=0.7430$ with the branch number N=2, or $d_{k+1}/d_k=0.6245$ with the branch number N=3. In a network with laminar, transitional, and turbulent flows considered simultaneously, the advantageous distribution of diameters and lengths of the individual branches is velocity-dependent and can be determined by computation for the minimal total pressure drop or power consumption.

To further maximize efficiency, several factors are taken into account:

Laminar, transitional, and turbulent flows are considered simultaneously

Pressure loss at the junction (bifurcation point) is considered

Shape of the tube can be considered

Additional constraints may be considered, such as, for example, mass, cost, covering area, etc.

A model of pressure drop versus flow rate was developed, where the total pressure drop is given by:

$$\Delta p_t = \sum_{i=1}^{4} \Delta p_i \quad (1)$$

where p is the pressure, $\Delta p_t$ is the total pressure drop of the system, and $\Delta p_i$ is the pressure drop through individual branches, and i is the branch level. In this case, a system having four levels of branches (where branch 1 is the primary parent level and 4 is the branch level with the smallest-diameter branches) was modeled.

Figure 15:
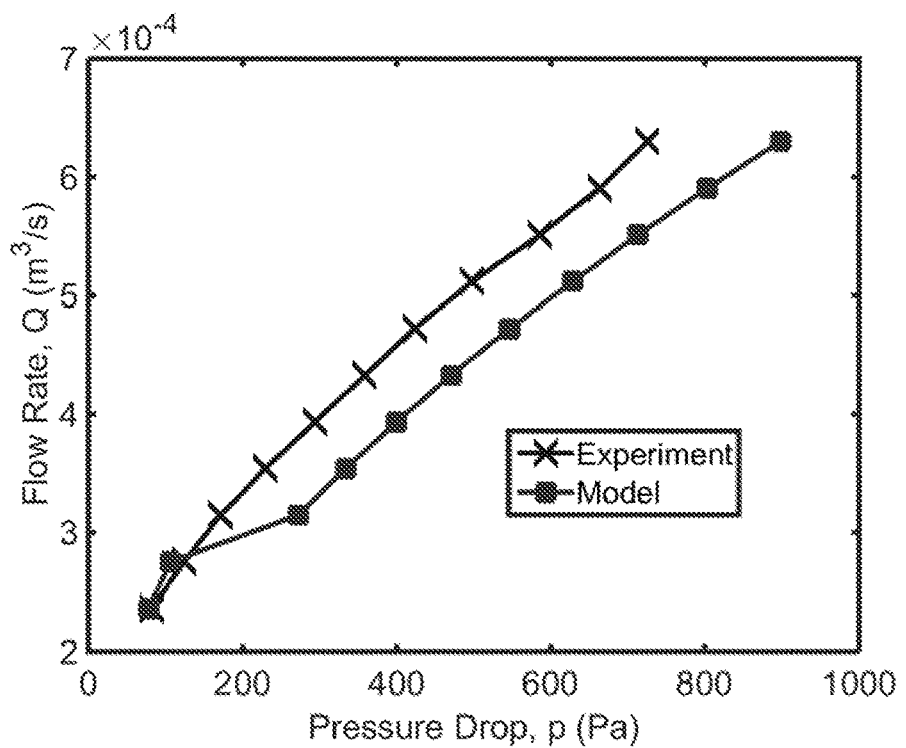
FIG. 15 is a chart showing agreement between experimental flow rate (y-axis) and pressure drop (x-axis) and modeled values.
Figure 16:
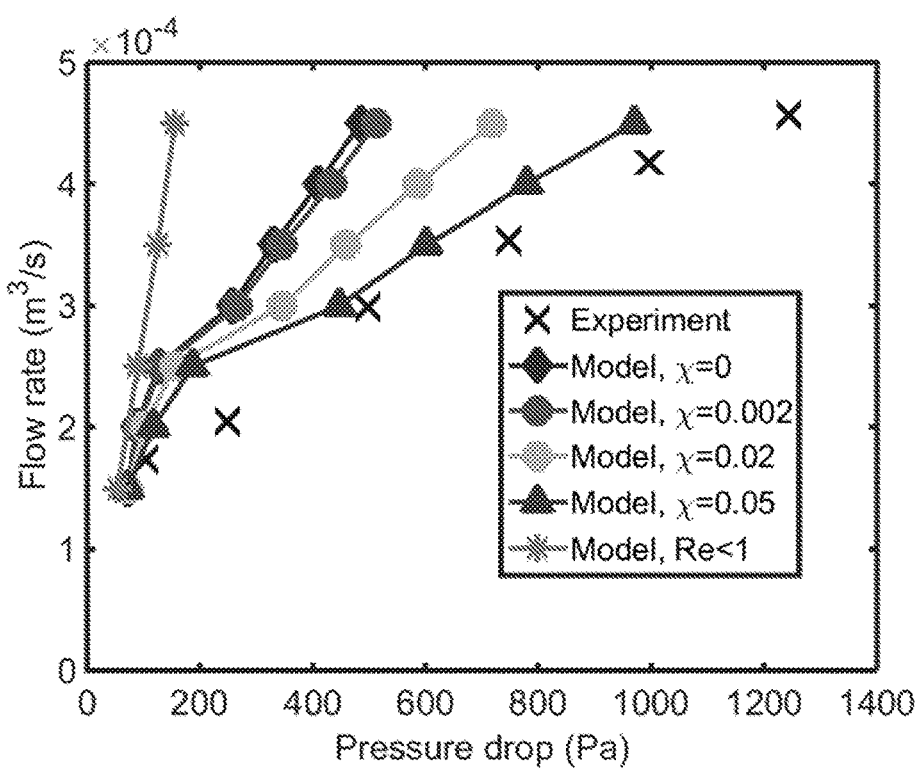
FIG. 16 is a chart showing the flow rate (y-axis) versus pressure drop (x-axis) for an experimental system and several models wherein the roughness is varied.
Figure 17:
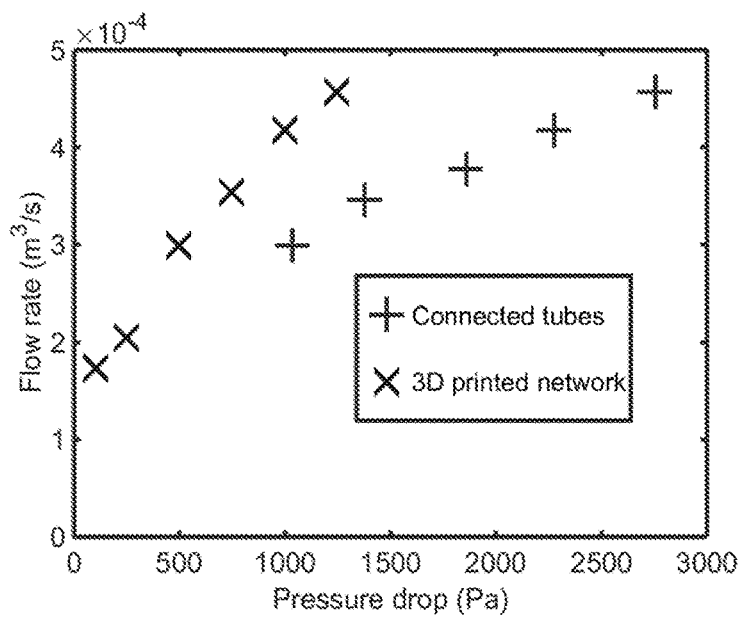
FIG. 17 is a chart showing the flow rate (y-axis) versus pressure drop (x-axis) for two tube networks according to the present disclosure—(1) a tube network with tubes connected by Y-shaped connectors; and (2) a 3D printed tube network.

The pressure drop in each sub-tube is a function of total flow rate:

$$\Delta p_i = f_{D,i} \frac{L_i}{D_i} \frac{\rho u_i^2}{2} \quad (2)$$

$$u_i = \frac{4 Q_i}{\pi D_i^2} = \frac{4}{\pi D_i^2} \frac{Q_t}{2^{i-1}} \quad (3)$$

where $f_D$ is the Darcy friction factor, L is the tube length, D is the tube diameter, $\rho$ is the gas density, u is the mean velocity, and Q is the flow rate. The Darcy friction factor for different flow types is determined by the Reynolds number (Re). For a. Laminar flow (Re<2300, HP Eq.):

$$f_{D,i} = \frac{64}{Re_i} \quad (4)$$

b. Transitional flow (2300<Re<4000)

$$f_{D,i} = \left\{ \left(\frac{64}{Re_i}\right)^8 + 9.5 \left[ \ln\left(\frac{\chi_i}{3.71} + \frac{5.8}{Re_i^{0.9}}\right) - \left(\frac{2500}{Re_i}\right)^6 \right]^{-16} \right\}^{0.125} \quad (5)$$

c. Turbulent flow (Re>4000)

$$\frac{1}{\sqrt{f_{D,i}}} = -2 \cdot lg\left[ \frac{2.51}{Re_i \sqrt{f_{D,i}}} + \frac{\chi}{3.71} \right] \quad (6)$$

$$Re_i = \frac{\rho u_i D_i}{\mu} \quad (7)$$

where $\chi$ is a roughness factor, and $\mu$ is the gas viscosity. The minimal total pressure drop can be found by varying the diameters and lengths of the individual branches. The minimal total power consumption, which is expressed as $\Delta W_t = \Sigma_{i=1}^{4} \Delta p_i Q_i$ can also be found by varying the diameters and lengths of the individual branches. Experimental data was measured and compared to the modeled data. In FIG. 15, a single tube was modeled to compare the agreement between the model and experimental data. In FIG. 16, experimental data from a 3D-printed tube is compared to the model with multiple values for roughness $\chi$. In FIG. 16, experimental data from a 3D printed tube network is compared to experimental data from a tube network having tubes connected by Y-shaped connectors.

Figure 18:
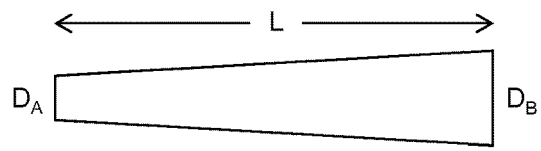
FIG. 18 is a diagram of a tube having a frusto-conical shape.
Figure 19:
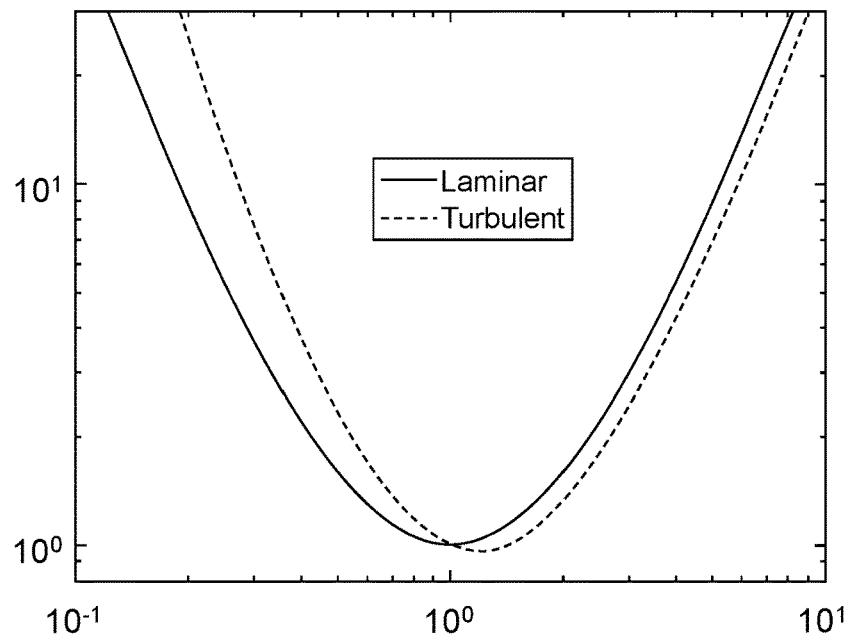
FIG. 19 is a chart depicting an advantageous diameter ratio, k, for laminar flows and turbulent flows in a frusto-conical tube, where $k=D_B/D_A$.

In some embodiments, the tubes of the tube network have a frustro-conical shape (see, for example, FIG. 18). The pressure drop per unit length for such conical tubes with a smooth inner wall is given by:

$$\left[\frac{\Delta p}{L}\right]_l = \frac{128\mu}{\pi} \frac{1}{3(D_A - D_B)} \left(\frac{1}{D_B^3} - \frac{1}{D_A^3}\right) = \frac{128\mu}{\pi D_A^4} \frac{1 + k + k^2}{3k^3} \quad (8)$$

$$\left[\frac{\Delta p}{L}\right]_t = a \frac{5}{19(D_A - D_B)} \left(\frac{1}{D_B^{19/5}} - \frac{1}{D_A^{19/5}}\right) = \frac{5a}{19} \frac{1}{1-k} \frac{1 - k^{19/5}}{k^{19/5}} \quad (9)$$

$$V = \frac{\pi D_{equ}^2 L}{4} = \frac{\pi L}{4} \frac{D_A^3 - D_B^3}{3(D_A - D_B)} = \frac{\pi L}{4} \frac{1 + k + k^2}{3} D_A^2 \quad (10)$$

where $D_A$ is the diameter of the tube at the small end of the tube, $D_B$ is the diameter at the large end of the tube, a is a constant, and $k = D_B/D_A$. An conical tube having advantageous diameter ratio k for reduced pressure drop was found to be k=1.18 (see FIG. 18). Embodiments of the tubes of the tube network may have a frusto-conical shape to enhance the performance of the presently-disclosed branched tube network. All of the tubes may have the same shape and/or size, or the tubes of a tube network may have different shapes and/or sizes from other tubes of the same tube network.

Figure 20:
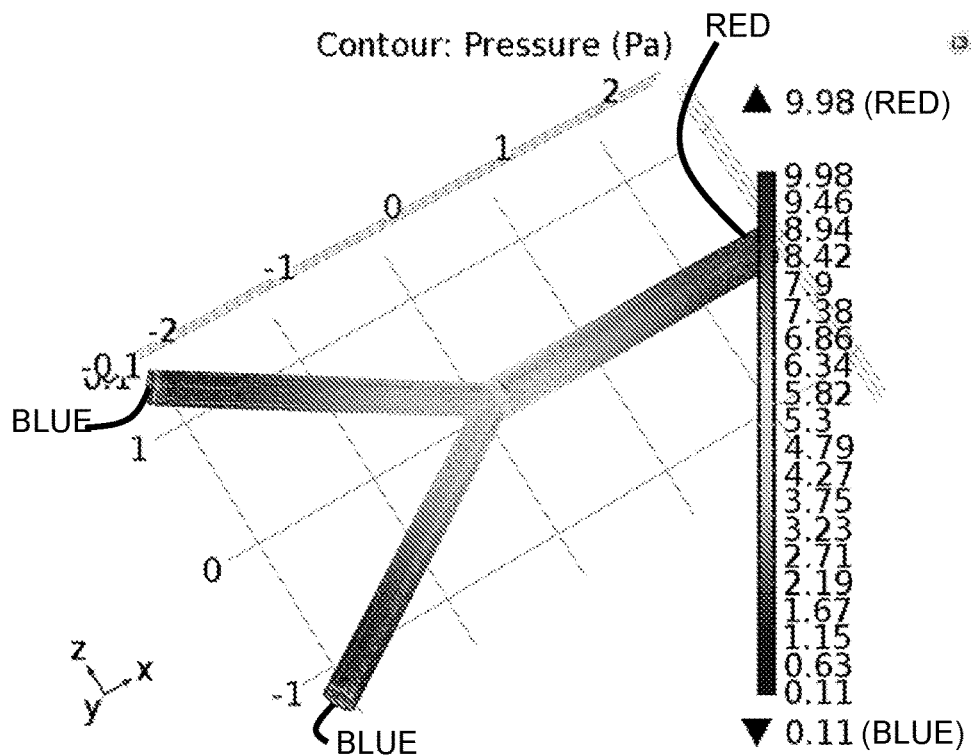
FIGS. 20-22 depict computer modeled data showing pressures in a Y-shaped connection of tubes.
Figure 21:
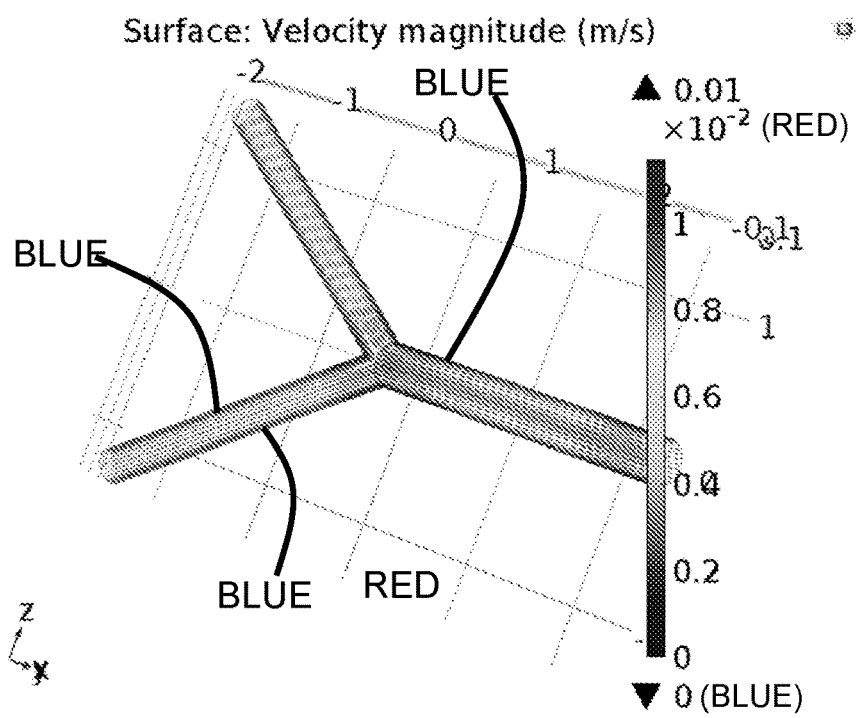
Figure 22:
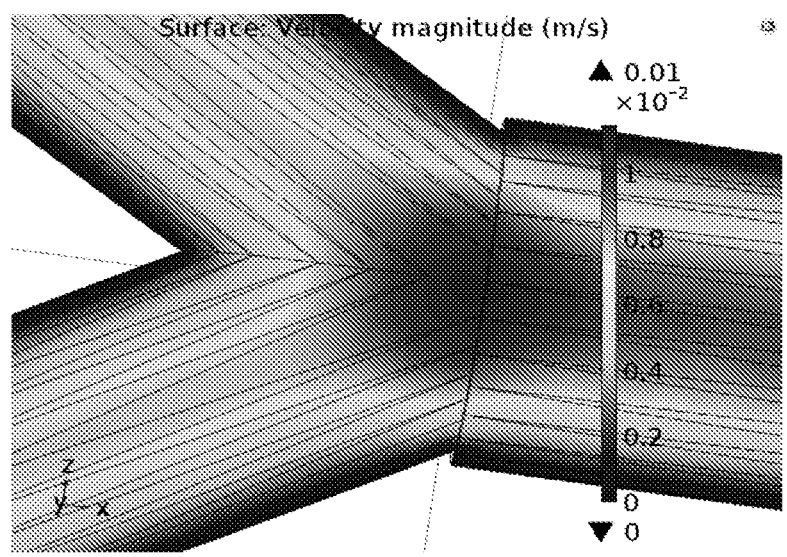

Next, the effect of the Y-junctions is considered, especially where turbulent flow exists. The pressure loss in the junction is dependent on the branching angle and the flow velocity. Simulation was used where the analytical solution was difficult to obtain (see FIGS. 20-22).

In some embodiments, such as the tube network 10 pictured in FIG. 3, working fluid introduced at the parent tube 12 is discharged through the ending daughter tubes 18. Other embodiments may be configured such that the fluid is collected through an inverse branched network such as the embodiments shown in FIGS. 10-12.

Figure 13:
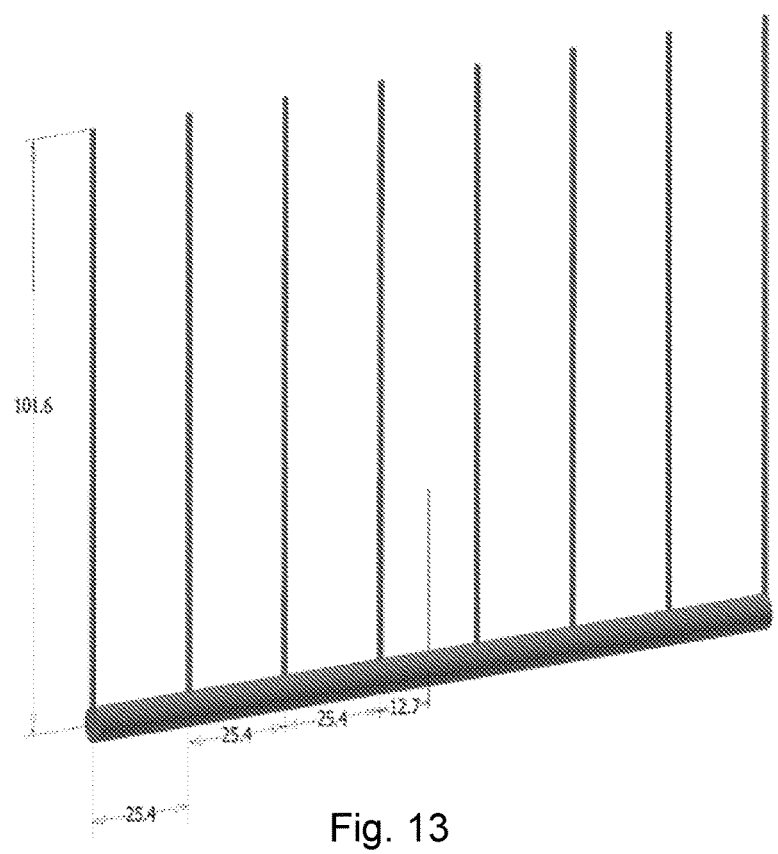
FIG. 13 is a schematic of a prior art tube system configured with a distribution header.
Figure 14:
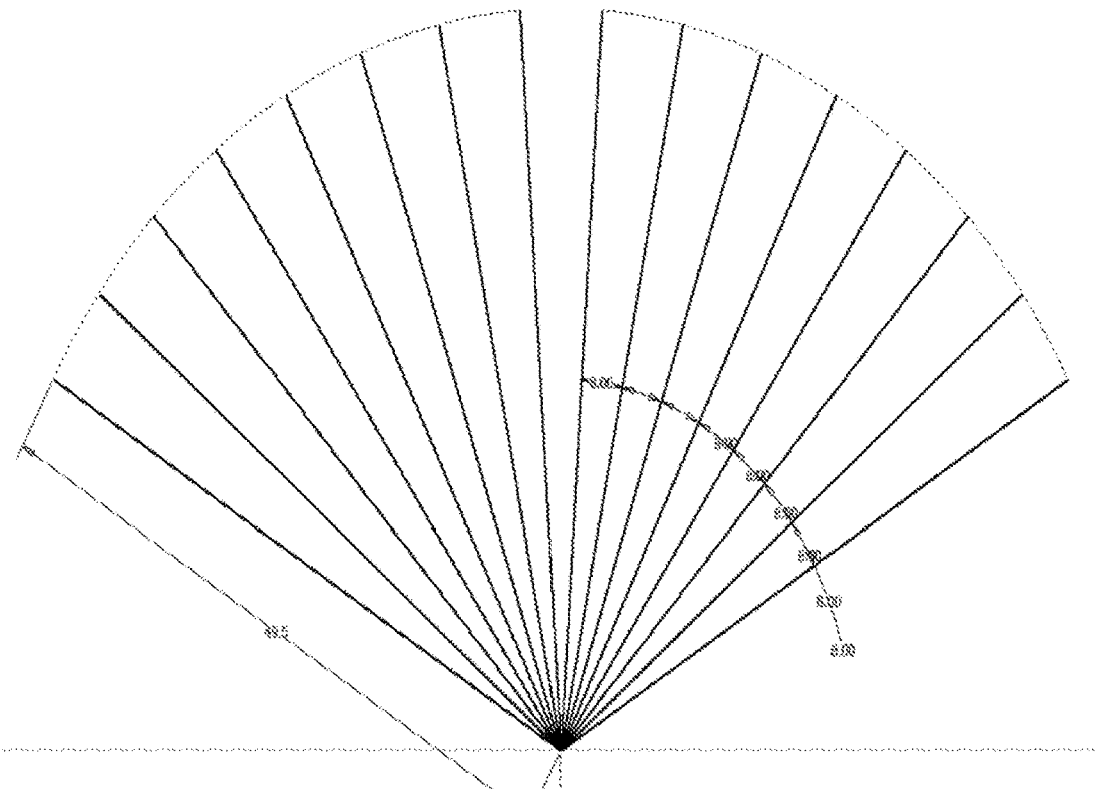
FIG. 14 is a schematic of a prior art hub-and-spoke tube system.

The use of multiple levels of bifurcations is shown to be advantageous over more traditional header-based configurations (FIG. 13) and single-level hub-and-spoke configured systems (FIG. 14). In particular, for a similar volume and length of tube, the presently-disclosed branched system has a lower pressure drop than systems configured with distribution headers or hub-and-spoke systems. For example, the pressure drop of a branched network is 29% of the pressure drop in a system configured with a distribution header (FIG. 13). In another example, the pressure drop of a branched network is approximately 62% of the pressure drop in a system having a hub-and-spoke design (FIG. 14).

Figure 23:
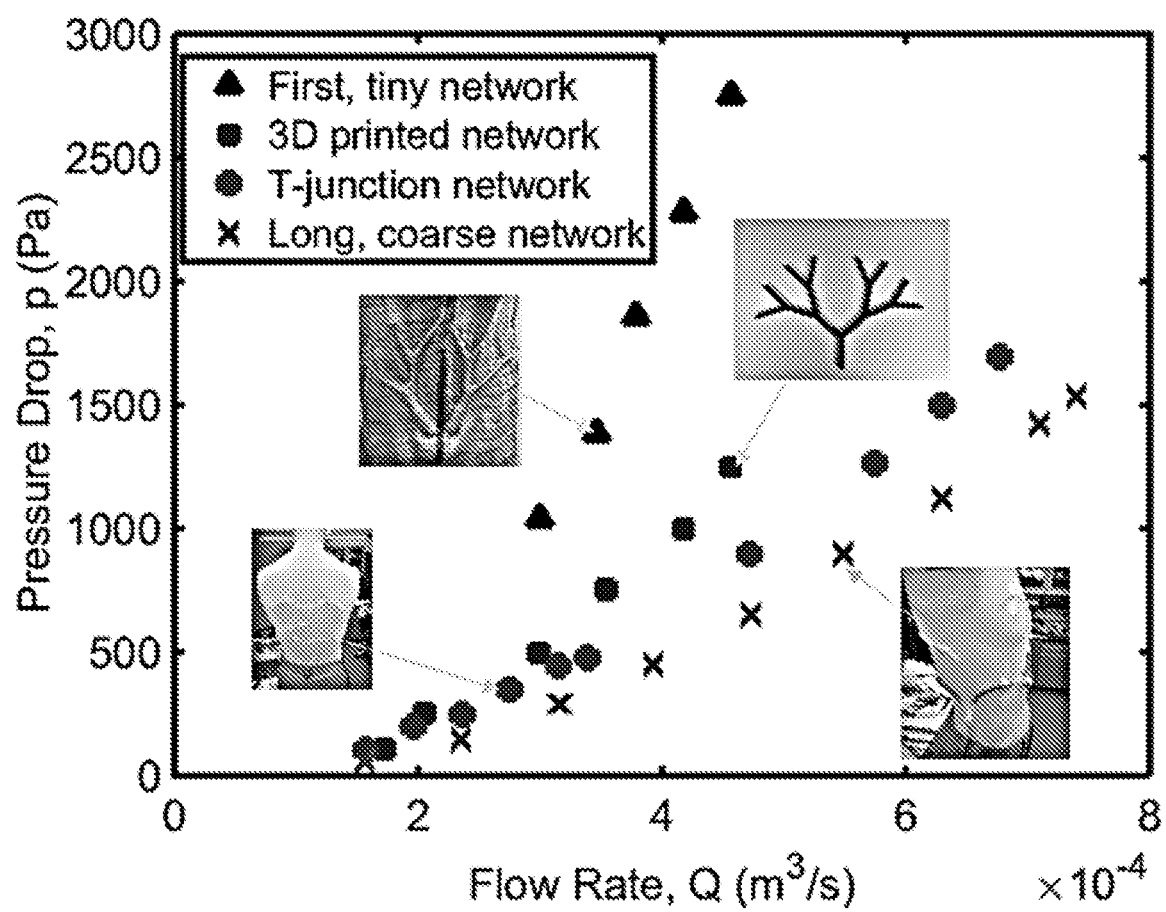
FIG. 23 is a chart depicting the flow resistance for different branched-tube network designs.

The flow resistance of several configurations of branched tube networks was measured (see FIG. 23). Of the initial test, the lowest pressure drop (250 Pa at a flow rate of $4 \times 10^{-4}$ m³/s) was found with a branched tube network constructed with Y-shaped junctions and tubes having an inner diameters of 6.35 mm and 5 mm. Compared with other branched tube networks, the T-junction branched tube network may be configured to have a more uniform flow around the body, yet with very low flow resistance, similar to the Y-junction (long, coarse network), which may have non-uniform flow around the body.

Garment Design

Figure 24:
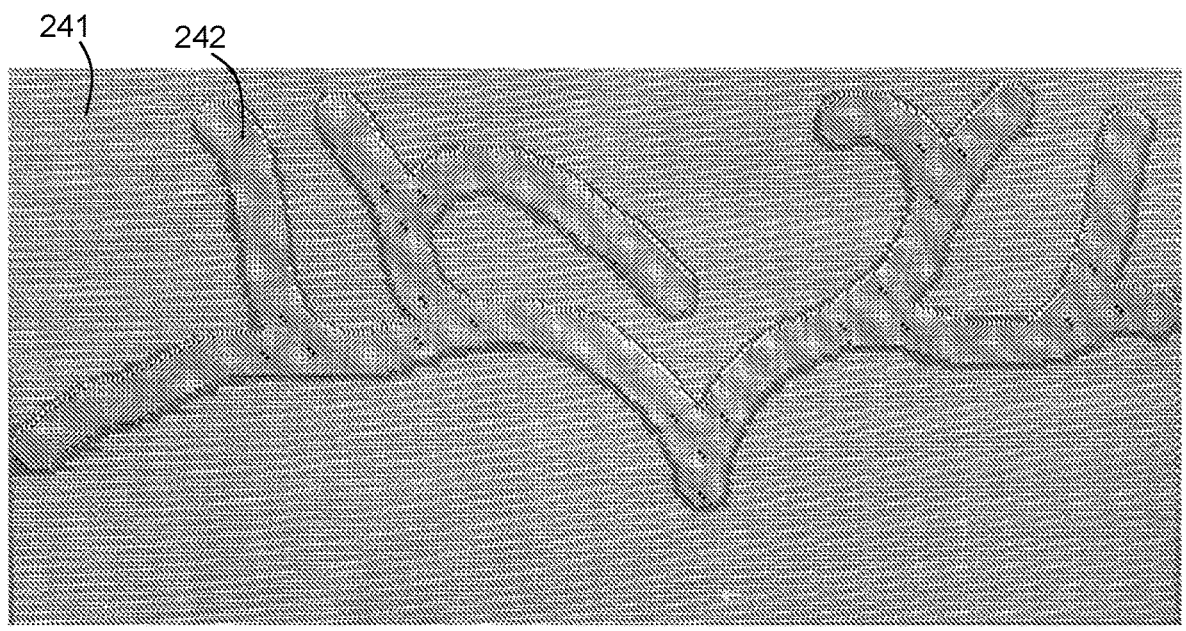
FIG. 24 depicts a test knit embodiment (fabric) using a mesh structure and single jersey tubular structure.

A knitted undershirt has been produced with channels for inserting a branched tube network as disclosed above (see FIGS. 2 and 3). The fabric used to make the prototype undershirt weighed 160 g/m2, which is typical for undershirt fabrics. A version of the knitted undershirt was made using cotton and Lycra® yarns. The use of Lycra improved stability and fit to the body. The undershirt was constructed with single jersey structure, but may have other structures such as, for example, a pique structure which may further improve the permeability and stability of the fabric. FIG. 24 shows another test embodiment used a knitting structure having a highly permeable mesh structure 241 and single jersey tubular structure 242.

The presently-disclosed garment may be particularly useful in business attire, sportswear, first responder apparel, and clothing for the elderly:

Business Attire:

Despite significant need for personal cooling and heating for office workers, the business outfit is a challenging application because jackets or shirts can easily cover the intake and/or exhaustion of air (where air is used as the working fluid) while office workers work in sedentary postures. Menswear business outfit designs were developed (see, for example, FIGS. 26A, 26B, 27A, and 27B) capable of accommodating proper operation of the thermoregulation systems of the garment while considering the following aspects:

accommodation of proper operation of the thermoregulation systems: limited or no negative influence over air flow through the energy conversion device and blower;

aesthetically acceptable, fashionable;

little or no change in normal dressing behavior;

ready access to thermoregulation components as needed; and the comfort of the wearer.

Figure 25:
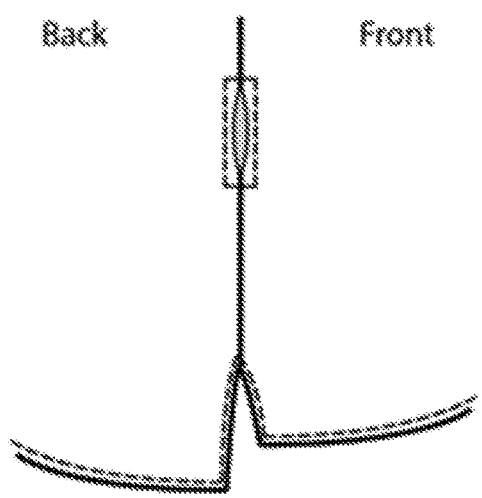
FIG. 25 shows an exemplary modification to a shirt for use with the present disclosure.
Figure 26A:
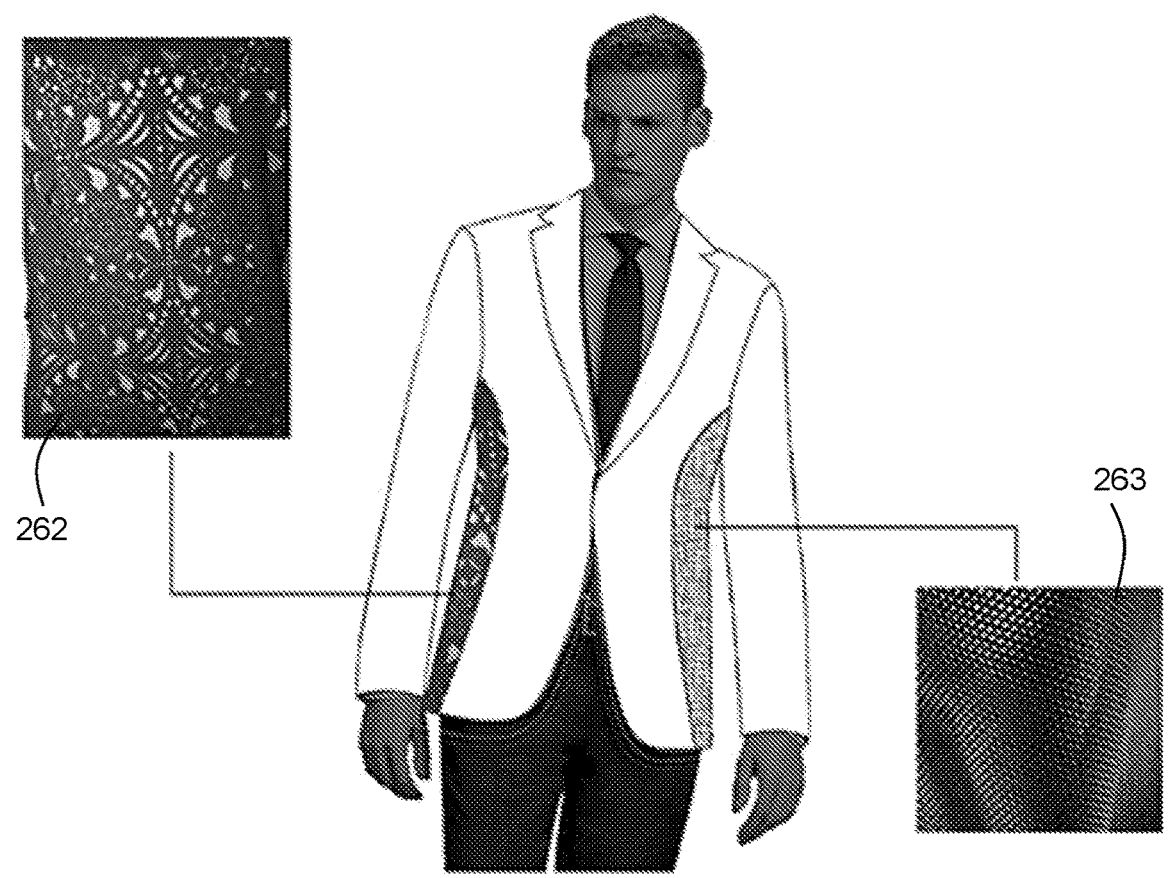
FIG. 26A shows a front view of an exemplary men's jacket designed for use with the present disclosure.
Figure 26B:
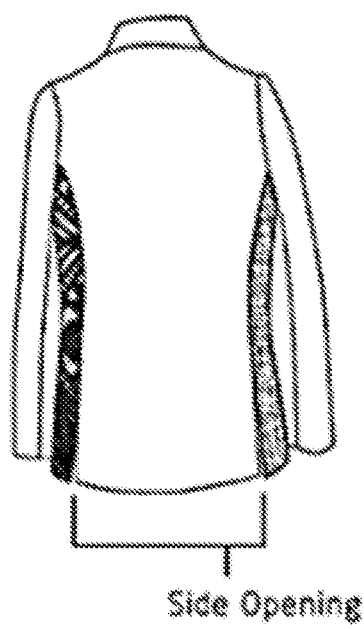
FIG. 26B shows the back view of the jacket of FIG. 26A
Figure 27A:
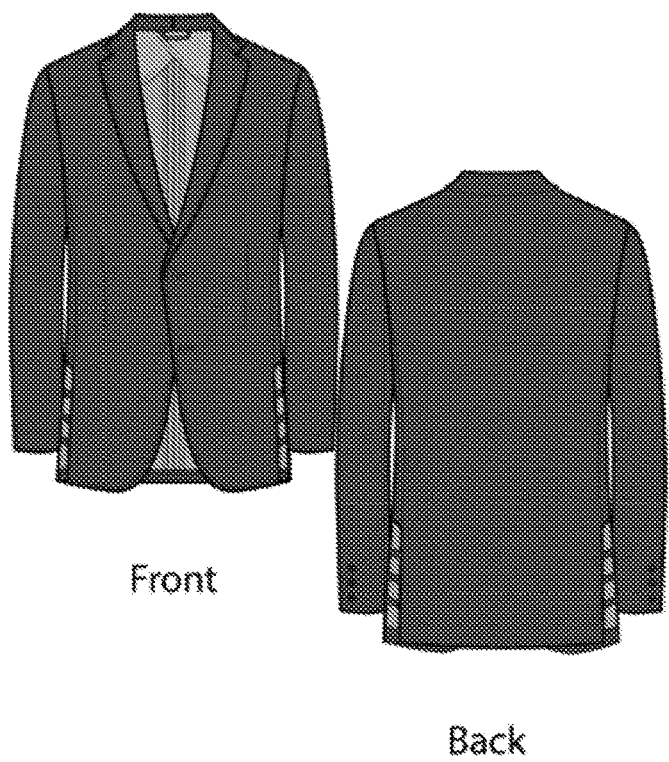
FIG. 27A shows a front and back view of a sketch of another exemplary jacket designed for use with the present disclosure.
Figure 27B:
FIG. 27B shows views of an exemplary jacket constructed to be similar to the sketches of FIG. 27A.

A traditional shirt design may utilize a small alteration by simply creating a button hole or long vents on a side seam, to allow connection between the EMD and the tube network within the garment (see FIG. 25). Such a design is highly feasible in mass production with minimal increase in labor cost.

A jacket design may require more significant modification of a side panel to allow sufficient air flow through the EMD while still providing an aesthetically acceptable and fashionable look. Two exemplary jacket designs were developed. The first jacket design includes laser cut side panels 262 or mesh fabrics 263 (see FIGS. 26A-26B). The use of a laser cut side panel 262 allows for easy access to the EMD, fashionable style, minimal changes in production, and sufficient air flow through the EMD. The second jacket design has a large opening in the side panel with decorative straps (see FIGS. 26A and 26B). This design also provides sufficient operation of and ready access to the EMD.

Figure 28A:
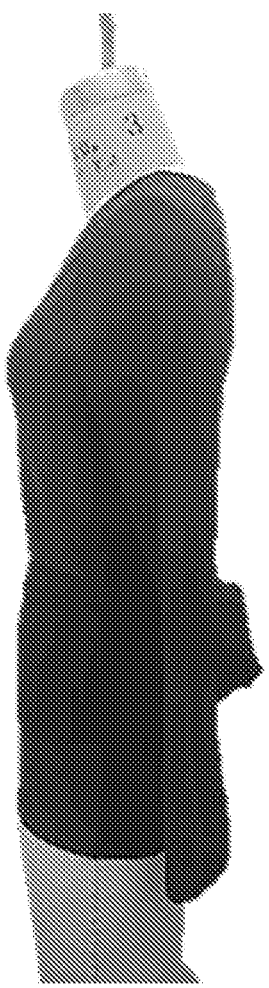
FIG. 28A show a side view of an exemplary dress for use suitable for use with the present disclosure.
Figure 28B:
FIG. 28B shows a detail view of the dress of FIG. 28A.
Figure 29A:
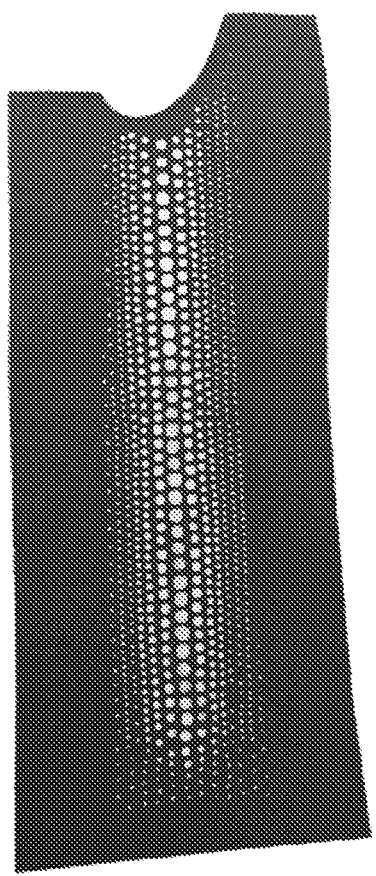
FIG. 29A shows an exemplary dress side panel for use with the present disclosure.
Figure 29B:
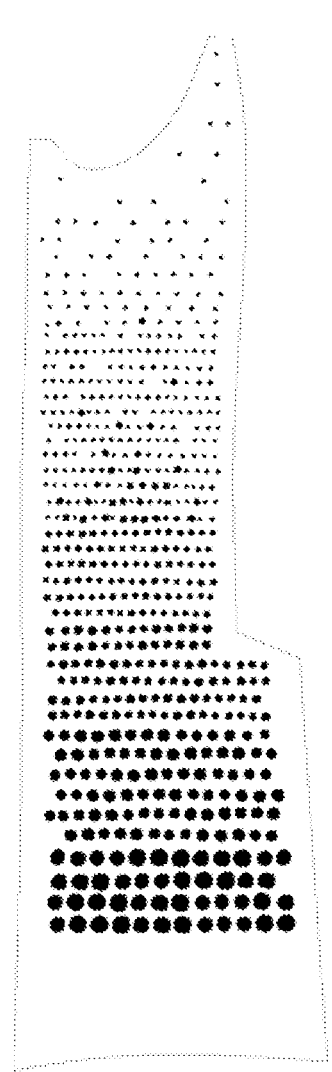
FIG. 29B shows an exemplary dress side panel for use with the present disclosure.
Figure 29C:
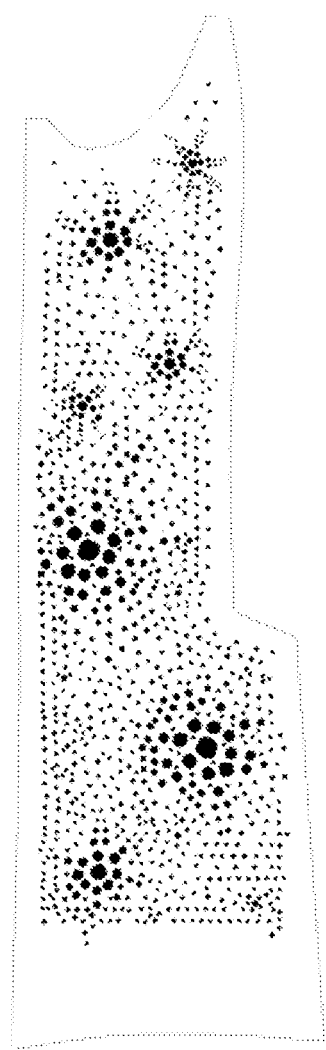
FIG. 29C shows an exemplary dress side panel for use with the present disclosure.

FIGS. 28A and 28B show a dress design that has been developed and produced. The dress was designed with mesh-covered pockets for holding the EMD and other components of the garment (see, FIG. 28B). In alternate designs, mesh or perforated side panels may be incorporated, examples of which are shown in FIGS. 29A-29C.

Sportswear:

In the athletic apparel applications, the EMD is preferably placed where there will be minimal impact by its presence. In such applications, it is advantageous to emphasize wearer mobility and comfort. The EMD can be mounted using straps, such as those used to mount cellphones to the upper arm during athletic activities. Such straps may be used on the upper arm, waist, thigh, or other areas where the presence will not interfere with activity. A length of tube may be increased where the EMD is mounted at a distance from the tube network (e.g., where the EMD is affixed to the thigh and the tube network is incorporated in an upper-body garment). Such straps, such as a waistband, may be capable of holding the EMD in place while also being adjustable depending on needs for specific body motions during athletic activities or physical training.

Figure 34:
FIG. 34 is a front view of a body armor vest for use in another embodiment of the present disclosure.
Figure 35:
FIG. 35 is a perspective view a waist pack for use in another embodiment of the present disclosure.
Figure 36:
FIG. 36 is a side view of exemplary military fatigues made according to the present disclosure.
Figure 37:
FIG. 37 is a detail view of a portion of the fatigues of FIG. 36.

First Responder & Military Applications:

Military personnel and law enforcement officers who are required to patrol assigned areas are good candidates for use of a garment of the present disclosure as they have need for thermal management under heat stress in outdoor environments. Those first responders do not generally have dramatic or extreme body movements during their duty, but have no ability to avoid heat stress. Considering characteristics of existing uniforms and load carriage system for military personnel and law enforcement officers, components of the presently-disclosed garment can easily be placed using the ubiquitous Modular Lightweight Load-carrying Equipment (MOLLE) system or other clip type mechanical structure. For example, a branched tube network and other components can be fitted to a ballistic vest such as that in FIG. 34. Similarly, components may be held using a waistband such as that shown in FIG. 35. An embodiment of the present disclosure has been produced using military-type fatigues (see FIGS. 36 and 37). FIG. 37 shows a pouch used to hold the EMD and controller.

Other Attire:

The use of various aforementioned mounts may be useful in applications outside of sportswear. For example, a garter-type thigh mount may be useful when donning formal wear such as, for example, a dress.

In another example, garments according to the present disclosure may be particularly suited for use by the elderly. Such individuals can be particularly sensitive to variances in ambient temperature. Through the use of an embodiment of the present garment, elderly individuals may be made comfortable according to their specific needs and preferences.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. A garment for regulating a temperature of a wearer, comprising:

a fabric configured to be worn by the wearer, the fabric having channels parallel to a primary surface of the fabric; and a branched tube network for circulating a working fluid, wherein the branched tube network is disposed in the channels of the fabric, the branched tube network comprising:

a plurality of tubes wherein at least one end of each tube of the plurality of tubes is branched and connected to at least two daughter tubes, the connection having a branch angle of between 1 and 359 degrees, inclusive;

wherein the tube network has at least two levels of branches; and wherein:
each tube is branched and connected to two daughter tubes, the branch angle being between 30 degrees and 60 degrees, inclusive; or
a diameter of the branched tube is greater than a diameter of the daughter tubes.

2. The garment of claim 1, wherein the each tube is branched and connected to two daughter tubes.

3. The garment of claim 2, wherein the branch angle is between 30 degrees and 60 degrees, inclusive.

4. The garment of claim 1, wherein a diameter of the branched tube is greater than a diameter of the daughter tubes.

5. The garment of claim 1, wherein the diameter of each daughter tube is between 60% and 80% of the branched tube.

6. The garment of claim 1, further comprising:
an energy conversion device for heating and/or cooling the working fluid; and
a blower in fluidic communication with the energy conversion device and the branched tube network for moving the working fluid.

7. The garment of claim 6, wherein a portion of the garment includes a mesh configured to cooperate with an intake of the blower.

8. The garment of claim 7, wherein the garment includes a pocket and the blower is disposed within the pocket.

9. The garment of claim 6, further comprising a controller in electronic communication with the blower, wherein the blower is controllable by the controller.

10. The garment of claim 9, further comprising one or more sensors in electronic communication with the controller, and wherein the controller is configured to regulate the blower according to a signal received from the one or more sensors.

11. The garment of claim 10, wherein a sensor of the one or more sensors is a temperature sensor.

12. The garment of claim 11, wherein the temperature sensor is configured to be positioned near the skin of the wearer.

13. The garment of claim 11, wherein the temperature sensor comprises a passive circuit wirelessly energized using radio frequency (RF) energy.

14. The garment of claim 13, wherein the passive circuit includes an RF antenna affixed to the fabric.

15. The garment of claim 14, wherein the RF antenna is embroidered onto the fabric.

16. The garment of claim 9, wherein the controller is configured to communicate with an environmental system.

17. The garment of claim 1, wherein the branched tube network is formed by 3D printing.

18. The garment of claim 1, wherein the tubes are perforated.

19. A branched tube network for a temperature regulating garment, comprising:

a parent tube having a branched end;
at least two daughter tubes, each daughter tube having a first end and a branched end, wherein the first end of each daughter tube is connected to the branched end of the parent tube;
at least two sets of at least two granddaughter tubes, each granddaughter tube having a first end connected to the branched end of a respective daughter tube such that the branched end of each daughter tube is connected to a set of at least two granddaughter tubes; and
wherein a diameter of the parent tube is greater than a diameter of the daughter tubes.

20. The branched tube network of claim 19, wherein the parent tube is connected to two daughter tubes, and each daughter tube is connected to two granddaughter tubes.

21. The branched tube network of claim 20, wherein the first end of each daughter tube is connected to the parent tube to form a branch angle between the daughter tubes, and the branch angle is between 1 and 359 degrees.

22. The branched tube network of claim 19, wherein a diameter of the daughter tubes is greater than a diameter of the granddaughter tubes.

23. The branched tube network of claim 19, wherein the granddaughter tubes are perforated.

24. A garment for regulating a temperature of a wearer, comprising:
a fabric configured to be worn by the wearer, the fabric having channels parallel to a primary surface of the fabric; and
a branched tube network according to claim 19 for circulating a working fluid, wherein the branched tube network is disposed in the channels of the fabric.

25. A garment for regulating a temperature of a wearer, comprising:
a fabric configured to be worn by the wearer, the fabric having channels parallel to a primary surface of the fabric;
a branched tube network for circulating a working fluid, wherein the branched tube network is disposed in the channels of the fabric, the branched tube network comprising:
a plurality of tubes wherein at least one end of each tube of the plurality of tubes is branched and connected to at least two daughter tubes, the connection having a branch angle of between 1 and 359 degrees, inclusive; and
wherein the tube network has at least two levels of branches;
an energy conversion device for heating and/or cooling the working fluid; and
a blower in fluidic communication with the energy conversion device and the branched tube network for moving the working fluid.

* * * * *